United States Patent [19]

Poletto et al.

[11] Patent Number: 4,599,204
[45] Date of Patent: Jul. 8, 1986

[54] OXALYLAMIDES USEFUL AS DENTAL ANTIPLAQUE AGENTS AND INHIBITORS OF CONNECTIVE TISSUE DESTRUCTION

[75] Inventors: John F. Poletto, Westwood, N.J.; Seymour Bernstein, New City, N.Y.

[73] Assignee: American Cyanamid Company, Stamford, Conn.

[21] Appl. No.: 711,112

[22] Filed: Mar. 11, 1985

[51] Int. Cl.$^4$ .................................... C07C 143/30
[52] U.S. Cl. ....................... 260/507 R; 560/139; 424/16; 424/38; 424/59; 424/69; 424/63
[58] Field of Search ............... 260/507 R; 560/139

[56] References Cited

U.S. PATENT DOCUMENTS

| | | | |
|---|---|---|---|
| 1,218,654 | 3/1917 | Heymann et al. | 260/506 |
| 1,308,071 | 7/1919 | Heymann et al. | 260/506 |
| 2,687,436 | 8/1954 | Novello | 568/328 |
| 3,626,008 | 12/1971 | Biland et al. | 260/507 R |
| 4,131,684 | 12/1978 | Bernstein et al. | 424/315 |
| 4,216,164 | 8/1980 | Bernstein | 260/506 |
| 4,216,165 | 8/1980 | Bernstein | 260/507 |
| 4,216,166 | 8/1980 | Bernstein | 260/507 |
| 4,297,372 | 10/1981 | Bernstein | 424/315 |

FOREIGN PATENT DOCUMENTS 856357 12/1960 United Kingdom.
1246141 9/1971 United Kingdom.

OTHER PUBLICATIONS

Moroz, L. A., *Thromb. Res.*, 10(4), 605 (1977).
Balaban, I. E. and King, H., *Journal of the Chemical Society*, 3068 (1927).

*Primary Examiner*—Nicky Chan
*Attorney, Agent, or Firm*—R. P. Raymond; G. C. Benson

[57] ABSTRACT

This invention concerns novel compounds useful in compositions and methods for preventing the attachment of dental plaque to the surfaces of the teeth of mammals and as inhibitors of connective tissue destruction. The compounds of this invention comprise certain [oxalylbis(iminophenylenecarbonylimino)]bis[hydroxynaphthalenesulfonic acids] and salts thereof which may be combined with pharmaceutically acceptable carriers or diluents to be administered in the form of conventional pharmaceutical compositions.

5 Claims, No Drawings

OXALYLAMIDES USEFUL AS DENTAL ANTIPLAQUE AGENTS AND INHIBITORS OF CONNECTIVE TISSUE DESTRUCTION

BACKGROUND OF THE INVENTION

1. Field of the Invention

The present invention relates to certain [oxalylbis-(iminophenylenecarbonylimino)]bis[hydroxynaphthalenesulfonic acids] and salts thereof, which are novel compounds useful as dental antiplaque agents and as inhibitors of connective tissue destruction.

2. Description of the Prior Art

Abnormal destruction of connective tissue by collagenase and/or neutral proteases causes tissue damage and/or tissue dysfunction. In these conditions an inhibitor of connective tissue destruction acting directly or indirectly would be useful in preventing, retarding, or reversing tissue damage and/or collagen diseases.

The term connective tissue refers to a matrix of at least three protein molecules, namely collagen, proteoglycan and elastin. These molecules play an important role in the structural integrity of normal tissues. Collagen, the most abundant protein in the body occupies a central position in the connective tissue matrix ["*Biochemistry of Collagen*", Ed. G. N. Ramachandran and A. H. Reddi, Academic Press, New York (1976); P. Bornstein, *Ann. Rev. Biochem.*, 43, 567 (1974); J. Fessler and L. Fessler, *Ann. Rev. Biochem.*, 47, 129 (1978)].

Collagen is, for example, the main structural component of the oral tissue (periodontal ligament, alveolar bone, gingiva, and cementum) [Fullmer, et al., *J. Dental Research*, 48, 646 (1969)]. Collagen amounts to 40% of cartilage protein, 90% of bone protein, and over 90% of dry dermis. Articular cartilage, the resilient tissue that covers the articulating extremities in synovial joints, consists of collagen fibers that are intimately meshed in a hydrated gel of proteoglycan.

Proteoglycan, as it exists in cartilage, is a molecule in which sulfated polysaccharide chains are covalently linked to a protein backbone ["*Dynamics of Connective Tissue Macromolecules*", Ed. P. M. Burleigh and A. R. Poole, North Holland, Amsterdam (1975)].

Elastin is a major connective tissue component of pulmonary structure ["*Elastin and Elastic Tissue*", Ed. L. B. Sandberg, W. R. Gray, and C. Franzblau, Plenum Press, New York (1977)]. The breakdown of elastin of pulmonary connective tissue is considered the primary event in pulmonary emphysema [A. Janoff in "Proteases and Biological Control", *Cold Spring Harbor Conference on Cell Proliferation*, 2, 603 (1975)].

Degradation of fibrous collagen is initiated by a combination of neutral proteases and tissue collagenase as an integral part of a complex immunopathological process which results in the loss of collagen from normal tissue. Under normal conditions cellular mechanisms maintain a careful balance between the rates of collagen synthesis and degradation. However, in certain pathological conditions, the ensuing elevated levels of neutral proteases and collagenase can result in rapid collagen degradation and tissue dysfunction. For example, in periodontal disease, the generated elevated levels of neutral proteases and collagenase in the gingival crevicular fluid rapidly degrade the fibrous collagen supporting the teeth. Periodontal pockets result ultimately from collagen degradation and, as these pockets deepen, support of the teeth is lost and alveolar bone is resorbed [K. Ohlsson, I. Ohlsson, and G. I. Basthall, *Acta Odontol. Scand.*, 32, 51 (1974); L. M. Golub, S. Kenneth, H. McEwan, J. B. Curran, and N. S. Ramamurthy, *J. Dental Research*, 55, 177 (1976); L. M. Golub, J. E. Stakin and D. L. Singer, *J. Dental Research*, 53, 1501 (1974); L. M. Wahl, S. M. Wahl, S. E. Mergenhagen, and G. R. Martin, *Proc. Natl. Acad. Sci. U. S.*, 71, 3598 (1974); *Science*, 187, 261 (1975)].

In arthritic conditions such as in rheumatoid arthritis, septic arthritis, and osteoarthritis, elevated degradation of collagen and proteoglycan initiate rapid destruction of articular tissue [J. M. Evanson, J. J. Jefferey, and S. M. Krane, *Science*, 158, 499 (1967); E. D. Harris, D. R. Dibona and, S. M. Krane, *J. Clin. Invest.*, 48, 2104 (1969); E. D. Harris in *Rheumatoid Arthritis*, Medcom. Press, N.Y. (1974); Z. Werb, C. L. Mainardi, C. A. Vater, and E. D. Harris, *New Eng. J. Med.*, 296, 1017 (1977); J. M. Dayer, R. G. Russell, and S. M. Krane, *Science*, 195, 181 (1977); E. D. Harris, C. A. Vater, C. L. Mainardi, and Z. Werb, *Agents and Actions*, 8, 35 (1978); D. E. Woolley, E. D. Harris, C. L. Mainardi, and C. E. Brinkerhoff, *Science*, 200, 773 (1978); E. D. Harris, C. S. Faulkner, F. E. Brown, *Clin. Orthoped.*, 110, 303 (1975); M. G. Ehrlich, H. J. Mankin, H. Jones, R. Wright, and C. Crisper, *J. Bone Jt. Surg.*, 57A, 565 (1975); S. Gordon, W. Newman, and B. Bloom, *Agents and Action*, 8, 19 (1978); "Mechanisms of Tissue Injury With Reference to Rheumatoid Arthritis", Ed. R. J. Perper, *Ann. N. Y. Acad. Sci.*, 256, 1-450 (1975)].

Increased collagen degradation in bone can result in abnormal bone destruction as in osteoporosis [C. G. Griffith, G. Nichols, J. D. Asher, and B. Flannagan, *J. Am. Med. Assoc.*, 193, 91 (1965); B. Gardner, H. Gray, and G. Hedyati, *Curr. Top. Surg. Res.*, 2, 175 (1970); B. Gardner, S. Wallach, H. Gray, and R. K. Baker, *Surg. Forum*, 22, 435 (1971)]. Collagenase activity has also resulted in tissue damage in cholesteatoma [M. Abramson, R. W. Schilling, C. C. Huang, and R. G. Salome, *Ann. Otol. Rhinol. Faryngol.*, 81, 158 (1975); M. Abramson and C. C. Huang, *Larynogoscope*, 77, 1 (1976)]. In corneal ulcerations that progress to loss of corneal integrity and function, collagenase has been implicated as a direct factor in corneal destruction [S. I. Brown, C. W. Hook, and N. P. Tragakis, *Invest. Ophthamol.*, 11, 149 (1972); M. B. Berman, C. H. Dohlman, P. F. Davison, and M. Ghadinger, *Exptl. Eye Res.*, 11, 225 (1971)]. Elevated levels of collagenase have also been observed in patients with epidermolysis bullosa and a group of related genetic diseases of the skin [E. A. Bauer, T. G. Dahl, and A. Z. Eisen, *J. Invest. Dermatology*, 68, 119 (1977).

Increased breakdown of elastin of the lung tissue by neutral proteases (elastase) may contribute to the lesions in pulmonary emphysema [I. Mandel, T. V. Darmle, J. A. Frierer, S. Keller, and G. M. Turino in *Elastin and Elastic Tissue*, Ed. L. B. Sandberg, W. R. Gray, and C. Franzblau, Plenum Press, N. Y., p 221 (1977)].

A variety of substances, both naturally occurring and synthetically prepared, have been found to be inhibitors of connective tissue destruction, e.g., inhibitors of collagen degradation, that is as collagenase inhibitors. Such substances include, for example, ethylenediaminetetraacetate, 1,10-phenanthroline, cysteine, dithiothreitol and sodium auriothiomalate [D. E. Woolley, R. W. Glanville, D. R. Roberts, and J. M. Evanson, *Biochem. J.*, 169, 265 (1978); S. Seifter and E. Harper, Chap. 18, "The Collagenases" in The Enzymes (3rd. Edition), 3, 649–697, Ed. by P. D. Boyer, Academic Press, N. Y. (1971)].

In the eye, a number of studies using collagenase inhibitors directly applied to corneal ulcerations have been reported. Calcium ethylenediaminetetraacetate and acetylcysteine reduce the frequency of ulceration in the alkali burned rabbit [M. Berman and C. Dohlman, *Arch. Ophthamol.*, 35, 95 (1975)]. Both cysteine and acetylcysteine have been effective in the treatment of acute and chronic corneal ulceration in the human, although the latter compound was preferred because of its greater stability [S. I. Brown, N. P. Tragakis and D. B. Pease, *Am. J. Opthalmol.*, 74, 316 (1972); M. Berman in *Trace Components of Plasma: Isolation and Clinical Significance*, 7th Annual Red Cross Symposium, p. 225, Alan R. Liss, Inc., N. Y. (1976)].

Naturally occurring collagenase inhibitors include the serum components $\alpha_2$-macroglobulin and $\beta_1$-anticollagenase [D. E. Woolley, R. W. Glanville, D. R. Roberts and J. M. Evanson, *Biochem. J.*, 169, 265 (1978)].

The deposition of dental plaque on teeth is considered to be a precursor to dental caries, gingivitis and periodontal disease. Therefore methods and compositions useful for the prevention, or inhibition of dental plaque formation on teeth are considered to be of major potential therapeutic importance.

Dental caries, which always begin on the external surfaces of the teeth, may be initiated by oral acidogenic bacteria which include *Lactobacillis acidophilus* and Streptococci, e.g., *Streptococcus mutans*, and yeasts capable of producing a pH of 5.5 or lower. Fermentable dietary carbohydrates serve as substrates for the microbial enzyme systems leading to the production of acidic metabolic products such as lactic, acetic, formic and butyric acids. Adherence of cariogenic bacteria such as *Streptococcus mutans*, and the like, to tooth enamel and their aggregation and colonization to dental plaque are prerequisites to the formation of carious lesions. Sucrose, cell wall polysaccharides, pellicle components of saliva and calcium, participate in the formation of the lesion. Colonization on the tooth surface may serve as an area favorable to the production of the acidic metabolic products hereinabove described, providing protection from the buffering action of the saliva and causing the dissolution of the enamel in the vicinity of the plaque area resulting in decalcification. Some proteolytic action on the organic structure may also take place.

Gingivitis, which is an inflammation of the gums characterized by congested, red and swollen gingivae, frequently may occur due to dental calculus as the sole cause.

Periodontitis, the most common form of periodontal disease is characterized by inflammatory tissue changes usually due to local irritation, which local causes include irritation resulting from calcareous deposits on the teeth.

In theory, dental caries can be prevented by eliminating cariogenic bacteria, especially *Streptococcus mutans*, from the mouth or by increasing the resistance of enamel to acid and/or the adherence of *S. mutans* to its surface.

Agents that bind to tooth components have, at least on a theoretical basis, a utility in the treatment of dental diseases [S. Hamada and H. D. Slade, *Microbiol. Rev.*, 44, 331 (1980)]. Support of this view is derived from results obtained with chlorohexidine [G. Rolla, H. Loe and C. R. Schiott, *Arch. Oral Biol.*, 16, 1109 (1971)]. These studies have shown that chlorohexidine, an antibacterial agent, binds to pellicle and/or tooth components and this binding may contribute, at least in part, to its long acting antigingivitis properties.

Fluoride, a known anticaries agent, is known to protect human tooth enamel from dissolution. Mechanistic studies indicate that fluoride binds to enamel and is incorporated into the hydroxyapatite fraction of the enamel. The resulting fluoroapatite is relatively resistant to acid.

U.S. Pat. No. 2,687,436 discloses substituted 3-(2-naphthyl)cyclohexanes useful in the treatment of collagen diseases. British Pat. Nos. 856,357 and 1,246,141, disclose 2-aryl-hexahydro-quinolizines and 1-hydroxylpraline derivatives, respectively, useful for treating diseases affecting connective tissue. The closest known structurally related compound to those of the present invention and disclosed as having collagenase inhibiting activity is found in *Thromb. Res.* 1977, 10(4), 605-11 wherein the trypanocidal agent trypan blue is reported as inhibiting the activity of collagenase, or a proteinase contaminant in the collagenase preparation. It is interesting, however, that in this same article, the ureide Suramin is reported as not inhibiting the action of collagenase. Ureides similar to those of the present invention, but not disclosed as inhibitors, are found in *Journal of the Chemical Society*, 3068 (1927), and in U.S. Pat. Nos. 1,218,654 and 1,308,071.

While some compounds may inhibit the destructive effect of collagenase on connective tissue by acting directly on collagenase itself, other compounds may inhibit such destruction by coating, binding or competing with sights on the connective tissue in such a manner as to prevent collagenase from attacking it. The present invention, however, is not to be restricted or limited to any particular mechanism or mode of action. Suffice it to say that the compounds of this invention have utility as inhibitors of connective tissue destruction albeit in whatever manner or mode.

SUMMARY OF THE INVENTION

This invention is concerned with the novel C-substituted naphthalenemonosulfonic oxalyldiimides which may be represented by Formula I:

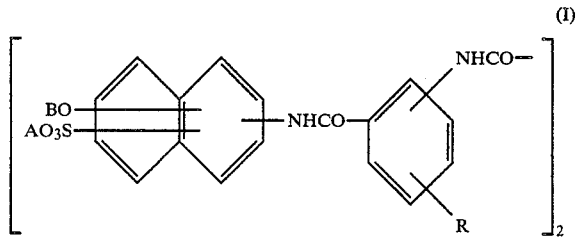

wherein A is hydrogen or a pharmaceutically acceptable salt cation; B is hydrogen, lower($C_1$-$C_6$)alkanoyl or alkali metal; and R is hydrogen or lower($C_1$-$C_3$)alkyl.

A preferred form of the present invention is concerned with those oxalyls wherein neither the R nor the NH— group are ortho to the fixed position of the carboxamido group (—NHCO—) in the bridgehead and such ureides may be represented by Formulae II, III and IV:

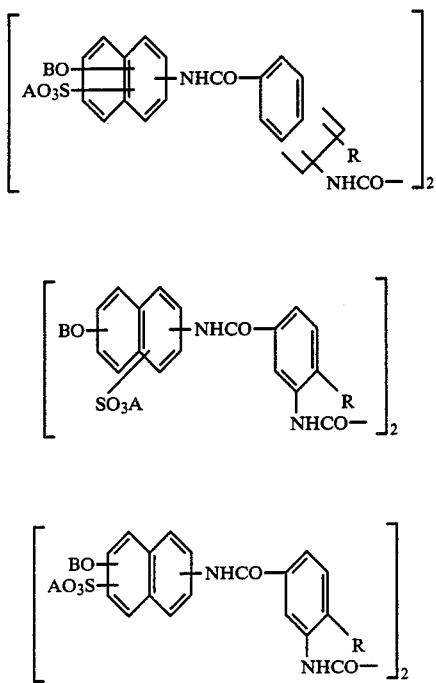

wherein A, B and R are as defined with reference to Formula I.

By pharmacologically acceptable salt cation is meant an alkali metal; an alkaline earth metal; ammonium; primary amine, e.g., ethylamine; secondary amine, e.g., diethylamine or diethanolamine; tertiary amine, e.g., pyridine, triethylamine or 2-dimethylaminomethyldibenzofuran; aliphatic amine, e.g., decamethylenediamine; or aromatic amine.

The novel [oxalylbis(iminophenylenecarbonylimino)]bis[hydroxynaphthalenesulfonic acids] and salts thereof of the present invention have been found to bind to various tooth components and also to inhibit the deposition of dental plaque onto the teeth of mammals.

The [oxalylbis(iminophenylenecarbonylimino)]bis[hydroxynaphthalenesulfonates] of this invention are substantially soluble in water or water/organic solvent vehicles and are applied to teeth by various means from different dentifrice formulations.

While the mechanism of action of these sulfonated derivatives in retarding plaque deposition is not known with certainty, the present invention is not to be restricted or limited to any particular mechanism or mode.

Representative compounds encompassed within this invention include, for example, 6,6'-[oxalylbis(imino-m-phenylenecarbonylimino)]bis[4-hydroxy-2-naphthalenesulfonic acid], disodium salt; 6,6'-[oxalylbis(imino-p-phenylenecarbonylimino)]bis[4-hydroxy-2-naphthalenesulfonic acid], disodium salt; 6,6'-[oxalylbis[(imino-6-methyl-3,1-phenylenecarbonyl)imino]]bis[4-hydroxy-2-naphthalenesulfonic acid], disodium salt; 6,6'-[oxalylbis[(imino-3-methyl-4,1-phenylenecarbonyl)imino]]bis[4-hydroxy-2-naphthalenesulfonic acid], disodium salt; 4,4'-[oxalylbis(imino-m-phenylenecarbonylimino)]bis[5-hydroxy-1-naphthalenesulfonic acid], disodium salt; 4,4'-[oxalylbis(imino-p-phenylenecarbonylimino)]bis[5-hydroxy-1-naphthalenesulfonic acid], disodium salt; 4,4'-[oxalylbis[(imino-6-methyl-3,1-phenylenecarbonyl)imino]]bis[5-hydroxy-1-naphthalenesulfonic acid], disodium salt; 4,4'-[oxalylbis[(imino-3-methyl-4,1-phenylenecarbonyl)imino] ]bis[5-hydroxy-1-naphthalenesulfonic acid], disodium salt; 3,3'-[oxalylbis(imino-m-phenylenecarbonylimino)]bis[4-hydroxy-2-naphthalenesulfonic acid], disodium salt; 3,3'-[oxalylbis(imino-p-phenylenecarbonylimino)]bis[4-hydroxy-2-naphthalenesulfonic acid], disodium salt; 3,3'-[oxalylbis[(imino-6-methyl-3,1-phenylenecarbonyl)imino]]bis[4-hydroxy-2-naphthalenesulfonic acid], disodium salt; 3,3'-[oxalylbis[(imino-3-methyl-4,1-phenylenecarbonyl)imino]]bis[4-hydroxy-2-naphthalenesulfonic acid], disodium salt; 6,6'-[oxalylbis(imino-m-phenylenecarbonylimino)]bis[5-hydroxy-1-naphthalenesulfonic acid], disodium salt; 6,6'-[oxalylbis(imino-p-phenylenecarbonylimino)]bis[5-hydroxy-1-naphthalenesulfonic acid], disodium salt; 6,6'-[oxalylbis[(imino-6-methyl-3,1-phenylenecarbonyl)imino]]bis[5-hydroxy-1-naphthalenesulfonic acid], disodium salt; 6,6'-[oxalylbis[(imino-3-methyl-4,1-phenylenecarbonyl)imino]]bis[5-hydroxy-1-naphthalenesulfonic acid], disodium salt; 3,3'-[oxalylbis(imino-m-phenylenecarbonylimino)]bis[4-hydroxy-1-naphthalenesulfonic acid], disodium salt; 3,3'-[oxalylbis(imino-p-phenylenecarbonylimino)]bis[4-hydroxy-1-naphthalenesulfonic acid], disodium salt; 3,3'-[oxalylbis[(imino-6-methyl-3,1-phenylenecarbonyl)imino]]bis[4-hydroxy-1-naphthalenesulfonic acid], disodium salt; 3,3'-[oxalylbis[(imino-3-methyl-4,1-phenylenecarbonyl)imino]]bis[4-hydroxy-1-naphthalenesulfonic acid], disodium salt; 6,6'-[oxalylbis(imino-m-phenyl-enecarbonylimino)]bis[5-hydroxy-2-naphthalenesulfonic acid], disodium salt; 6,6'-[oxalylbis(imino-p-phenylenecarbonylimino)]bis[5-hydroxy-2-naphthalenesulfonic acid], disodium salt; 6,6'-[oxalylbis[(imino-6-methyl-3,1-phenylenecarbonyl)imino]]bis[5-hydroxy-2-naphthalenesulfonic acid], disodium salt; 6,6'-[oxalylbis[(imino-3-methyl-4,1-phenylenecarbonyl)imino]]bis[5-hydroxy-2-naphthalenesulfonic acid], disodium salt; 7,7'-[oxalylbis(imino-m-phenylenecarbonylimino)]bis[8-hydroxy-2-naphthalenesulfonic acid], disodium salt; 7,7'-[oxalylbis(imino-p-phenylenecarbonylimino)]bis[8-hydroxy-2-naphthalenesulfonic acid], disodium salt; 7,7'-[oxalylbis[(imino-6-methyl-3,1-phenylenecarbonyl)imino]]bis[8-hydroxy-2-naphthalenesulfonic acid], disodium salt; 7,7'-[oxalylbis[(imino-3-methyl-4,1-phenylenecarbonyl)imino]]bis[8-hydroxy-2-naphthalenesulfonic acid], disodium salt; 7,7'-[oxalylbis(imino-m-phenylenecarbonylimino)]bis[8-hydroxy-1-naphthalenesulfonic acid], disodium salt; 7,7'-[oxalylbis(imino-p-phenylenecarbonylimino)]bis[8-hydroxy-1-naphthalenesulfonic acid], disodium salt; 7,7'-[oxalylbis[(imino-6-methyl-3,1-phenylenecarbonyl)imino]]bis[8-hydroxy-1-naphthalenesulfonic acid], disodium salt; 7,7'-oxalylbis[(imino-3-methyl-4,1-phenylenecarbonyl)imino]]bis[8-hydroxy-1-naphthalenesulfonic acid], disodium salt; 7,7'-[oxalylbis(imino-m-phenylenecarbonylimino)]bis[5-hydroxy-1-naphthalenesulfonic acid], disodium salt; 7,7'-[oxalylbis(imino-p-phenylenecarbonylimino)]bis[5-hydroxy-1-naphthaleneesulfonic acid], disodium salt; 7,7'-[oxalylbis[(imino-6-methyl-3,1-phenylenecarbonyl)imino]]bis[5-hydroxy-1-naphthalenesulfonic acid], disodium salt; 7,7'-[oxalylbis[(imino-3-methyl-4,1-phenylenecarbonyl)imino]]bis[5-hydroxy-1-naphthalenesulfonic acid], disodium salt; 7,7'-[oxalylbis(imino-m-phenylenecarbonylimino)]bis[5-hydroxy-2-naphthalenesulfonic acid], disodium salt; 7,7'-[oxalylbis(imino-p-phenylenecarbonylimino)]bis[5-hydroxy-2-naphthalenesulfonic acid], disodium salt; 7,7'-[oxalylbis[(imino-6-methyl-3,1-phenylenecarbonyl)imino]]bis[5-hydroxy-2-naphthalenesulfonic acid], disodium salt; 7,7'-[oxalylbis[(imino-3-methyl-4,1-phenylenecarbonyl)imino]]bis[5-hydroxy-2-naphthalenesulfonic acid], disodium salt; 6,6'-[oxalylbis(imino-m-phenylenecarbonylimino)]bis[8-hydroxy-2-naphthalenesulfonic acid], disodium salt; 6,6'-[oxalylbis(imino-p-phenylenecarbonylimino)]bis[8-hydroxy-2-naphthalenesulfonic acid], disodium salt; 6,6'-[oxalylbis[(imino-6-methyl-3,1-phenylenecarbonyl)imino]]bis[8-hydroxy-2-naphthalenesulfonic acid], disodium salt; 6,6'-[oxalylbis[(imino-3-methyl-4,1-phenylenecarbonyl)imino]]bis[8-hydroxy-2-naphthalenesulfonic acid], disodium salt; 4,4'-[oxalylbis(imino-m-phenylenecarbonylimino)] bis[1-hydroxy-2-naphthalenesulfonic acid], disodium salt; 4,4'-[oxalylbis(imino-p-phenylenecarbonylimino)]bis[1-hydroxy-2-naphthalenesulfonic acid], disodium salt; 4,4'-[oxalylbis[(imino-6-methyl-3,1-phenylenecarbonyl)imino]]bis[1-hydroxy-2-naphthalenesulfonic acid], disodium salt; 4,4'-[oxalylbis[(imino-3-methyl-4,1-phenylenecarbonyl)imino]]bis[1-hydroxy-2-naphthalenesulfonic acid], disodium salt; 1,1'-[oxalylbis(imino-m-phenylenecarbonylimino)]bis[4-hydroxy-2-naphthalenesulfonic acid], disodium salt; 1,1'-[oxalylbis(imino-p-phenylenecarbonylimino)]bis[4-hydroxy-2-naphthalenesulfonic acid], disodium salt; 1,1'-[oxalylbis[(imino-6-methyl-3,1-phenylenecarbonyl)imino]]bis[4-hydroxy-2-naphthalenesulfonic acid], disodium salt; 1,1'-[oxalylbis[(imino-3-methyl-4,1-phenylenecarbonyl)imino]]bis[4-hydroxy-2-naphthalenesulfonic acid], disodium salt; 8,8'-[oxalylbis(imino-m-phenylenecarbonylimino)]bis[5-hydroxy-1-naphthalenesulfonic acid], disodium salt; 8,8'-[oxalylbis(imino-p-phenylenecarbonylimino)]bis[5-hydroxy-1-naphthalenesulfonic acid], disodium salt; 8,8'-[oxalylbis[(imino-6-methyl-3,1-phenylenecarbonyl)imino]]bis[5-hydroxy-1-naphthalenesulfonic acid], disodium salt; 8,8'-[oxalylbis[(imino-3-methyl-4,1-phenylenecarbonyl)imino]]bis[5-hydroxy-1-naphthalenesulfonic acid], disodium salt; 8,8'-[oxalylbis(imino-m-phenylenecarbonylimino)]bis[5-hydroxy-2-naphthalenesulfonic acid], disodium salt; 8,8'-[oxalylbis(imino-p-phenylenecarbonylimino)]bis[5-hydroxy-2-naphthalenesulfonic acid], disodium salt; 8,8'-[oxalylbis[(imino-6-methyl-3,1-phenylenecarbonyl)imino]]bis[5-hydroxy-2-naphthalenesulfonic acid], disodium salt; 8,8'-[oxalylbis[(imino-3-methyl-4,1-phenylenecarbonyl)imino]]bis[5-hydroxy-2-naphthalenesulfonic acid], disodium salt; 5,5'-[oxalylbis(imino-m-phenylenecarbonylimino)]bis[8-hydroxy-2-naphthalenesulfonic acid], disodium salt; 5,5'-[oxalylbis(imino-p-phenylenecarbonylimino)]bis[8-hydroxy-2-naphthalenesulfonic acid], disodium salt; 5,5'-[oxalylbis[(imino-6-methyl-3,1-phenylenecarbonyl)imino]]bis[8-hydroxy-2-naphthalenesulfonic acid], disodium salt; 5,5'-[oxalylbis[(imino-3-methyl-4,1-phenylenecarbonyl)imino]]bis[8-hydroxy-2-naphthalenesulfonic acid], disodium salt; 5,5'-[oxalylbis(imino-m-phenylenecarbonylimino)]bis[8-hydroxy-1-naphthalenesulfonic acid], disodium salt; 5,5'-[oxalylbis(imino-p-phenylenecarbonylimino)]bis[8-hydroxy-1-naphthalenesulfonic acid], disodium salt; 5,5'-[oxalylbis[(imino-6-methyl-3,1-phenylenecarbonyl)imino]]bis[8-hydroxy-1-naphthalenesulfonic acid], disodium salt; 5,5'-[oxaalylbis[(imino-3-methyl-4,1-phenylenecarbonyl)imino]]bis[8-hydroxy-1-naphthalenesulfonic acid], disodium salt; 5,5'-[oxalylbis(imino-m-phenylenecarbonylimino)]bis[1-hydroxy-2-naphthalenesulfonic acid], disodium salt; 5,5'-[oxalylbis(imino-p-phenylenecarbonylimino)]bis[1-hydroxy-2-naphthalenesulfonic acid], disodium salt; 5,5'-[oxalylbis[,(imino-6-methyl-3,1-phenylenecarbonyl)imino]]bis[1-hydroxy-2-naphthalenesulfonic acid], disodium salt; 5,5'-[oxalylbis[(imino-3-methyl-4,1-phenylenecarbonyl)imino]]bis[1-hydroxy-2-naphthalenesulfonic acid], disodium salt; 8,8'-[oxalylbis(imino-m-phenylenecarbonylimino)]bis[4-hydroxy-2-naphthalenesulfonic acid], disodium salt; 8,8'-[oxalylbis(imino-p-phenylenecarbonylimino)]bis[4-hydroxy-2-naphthalenesulfonic acid], disodium salt; 8,8'-[oxalylbis[(imino-6-methyl-3,1-phenylenecarbonyl)imino]]bis[4-hydroxy-1-naphthalenesulfonic acid], disodium salt; 8,8'-[oxalylbis[(imino-3-methyl-4,1-phenylenecarbonyl)imino]]bis[4-hydroxy-2-naphthalenesulfonic acid], disodium salt; 8,8'-[oxalylbis(imino-m-phenylenecarbonylimino)]bis[4-hydroxy-1-naphthalenesulfonic acid], disodium salt; 8,8'-[oxalylbis(imino-p-phenylenecarbonylimino)]bis[4-hydroxy-1-naphthalenesulfonic acid], disodium salt; 8,8'-[oxalylbis[(imino-6-methyl-3,1-phenylnecarbonyl)imino]]bis[4-hydroxy-1-naphthalenesulfonic acid], disodium salt; 8,8'-[oxalylbis[(imino-3-methyl-4,1-phenylenecarbonyl)imino]]bis[4-hydroxy-1-naphthalenesulfonic acid], disodium salt; 1,1'-[oxalylbis(imino-m-phenylenecarbonylimino)]bis[5-hydroxy-2-naphthalenesulfonic acid], disodium salt; 1,1'-[oxalylbis(imino-p-phenylenecarbonylimino)] bis[5-hydroxy-2-naphthalenesulfonic acid], disodium salt; 1,1'-[oxalylbis[(imino-6-methyl-3,1-phenylenecarbonyl)imino]]bis[5-hydroxy-2-naphthalenesulfonic acid], disodium salt; 1,1'-[oxalylbis[(imino-3-methyl-4,1-phenylenecarbonyl)imino]]bis[5-hydroxy-2-naphthalenesulfonic acid], disodium salt; 4,4'-[oxalylbis(imino-m-phenylenecarbonylimino)]bis[8-hydroxy-1-naphthalenesulfonic acid], disodium salt; 4,4'-[oxalylbis(imino-p-phenylenecarbonylimino)]bis[8-hydroxy-1-naphthalenesulfonic acid], disodium salt; 4,4'-[oxalylbis[(imino-6-methyl-3,1-phenylenecarbonyl)imino]]bis[8-hydroxy-2-naphthalenesulfonic acid], disodium salt; 4,4'-[oxalylbis[(imino-3-methyl-4,1-phenylenecarbonyl)imino]]bis[8-hydroxy-1-naphthalenesulfonic acid], disodium salt; 6,6'-[oxalylbis(imino-m-phenylenecarbonylimino)]bis[1-hydroxy-2-naphthalenesulfonic acid], disodium salt; 6,6'-[oxalylbis(imino-p-phenylenecarbonylimino)]bis[1-hydroxy-2-naphthalenesulfonic acid], disodium salt; 6,6'-[oxalylbis[(imino-6-methyl-3,1-phenylenecarbonyl)imino]]bis[1-hydroxy-2-naphthalenesulfonic acid], disodium salt; 6,6'-[oxalylbis[(imino-3-methyl-4,1-phenylenecarbonyl)imino]]bis[1-hydroxy-2-naphthalenesulfonic acid], disodium salt; 7,7'-[oxalylbis(imino-m-phenylenecarbonylimino)]bis[4-hydroxy-2-naphthalenesulfonic acid], disodium salt; 7,7'-[oxalylbis(imino-p-phenylenecarbonylimino)]bis[4-hydroxy-2-naphthalenesulfonic acid], disodium salt; 7,7'-[oxalylbis[(imino-6-methyl-3,1-phenylenecarbonyl)imino]]bis[4-hydroxy-2-naphthalenesulfonic acid], disodium salt; 7,7'-[oxalylbis[(imino-3-methyl-4,1-phenylenecarbonyl)imino]]bis[4-hydroxy-2-naphthalenesulfonic acid], disodium salt; 7,7'-[oxalylbis(imino-m-phenylenecarbonylimino)]bis[4-hydroxy-1-naphthalenesulfonic acid], disodium salt; 7,7'-[oxalylbis(imino-p-phenylenecarbonylimino)]bis[4-hydroxy-1-naphthalenesulfonic acid], disodium salt; 7,7'-[oxalylbis[(imino-6-methyl-3,1-phenylenecarbonyl)imino]]bis[4-hydroxy-1-naphthalenesulfonic acid], disodium salt; 7,7'-[oxalylbis[(imino-3-methyl-4,1-phenylenecarbonyl)imino]]bis[4-hydroxy-1-naphthalenesulfonic acid], disodium salt; 2,2'-[oxalylbis(imino-m-phenylenecarbonylimino)]bis[5-hydroxy-1-naphthalenesulfonic acid], disodium salt; 2,2'-[oxalylbis(imino-p-phenylenecarbonylimino)]- bis[5-hydroxy-1-naphthalenesulfonic acid], disodium salt; 2,2'-[oxalylbis[(imino-6-methyl-3,1-phenylenecarbonyl)imino]]bis[5-hydroxy-1-naphthalenesulfonic acid], disodium salt; 2,2'-[oxalylbis[(imino-3-methyl-4,1-phenylenecarbonyl)imino]]bis[5-hydroxy-1-naphthalenesulfonic acid], disodium salt; 8,8'-[oxalylbis(imino-m-phenylenecarbonylimino)]bis[1-hydroxy-2-naphthalenesulfonic acid], disodium salt; 8,8'-[oxalylbis(imino-p-phenylenecarbonylimino)]bis[1-hydroxy-2-naphthalenesulfonic acid], disodium salt; 8,8'-[oxalylbis[(imino-6-methyl-3,1-phenylenecarbonyl)imino]]bis[1-hydroxy-2-naphthalenesulfonic acid], disodium salt; 8,8'-[oxalylbis[(imino-3-methyl-4,1-phenylenecarbonyl)imino]]bis[1-hydroxy-2-naphthalenesulfonic acid], disodium salt; 5,5'-[oxalylbis(imino-m-phenylenecarbonylimino)]bis[4-hydroxy-2-naphthalenesulfonic acid], disodium salt; 5,5'-[oxalylbis(imino-p-phenylenecarbonylimino)]bis[4-hydroxy-2-naphthalenesulfonic acid], disodium salt; 5,5'-[oxalylbis[(imino-6-methyl-3,1-phenylenecarbonyl)imino]]bis[4-hydroxy-2-naphthalenesulfonic acid], disodium salt; 5,5'-[oxalylbis[(imino-3-methyl-4,1-phenylenecarbonyl)imino]]bis[4-hydroxy-2-naphthalenesulfonic acid], disodium salt; 5,5'-[oxalylbis(imino-m-phenylenecarbonylimino)]bis[4-hydroxy-1-naphthalenesulfonic acid], disodium salt; 5,5'-[oxalylbis(imino-p-phenylenecarbonylimino)]bis[4-hydroxy-1-naphthalenesulfonic acid], disodium salt; 5,5'-[oxalylbis[(imino-6-methyl-3,1-phenylenecarbonyl)imino]]bis[4-hydroxy-1-naphthalenesulfonic acid], disodium salt; 5,5'-[oxalylbis[(imino-3-methyl-4,1-phenylenecarbonyl)imino]]bis[4-hydroxy-1-naphthalenesulfonic acid], disodium salt; 4,4'-[oxalylbis(imino-m-phenylenecarbonylimino)]bis[5-hydroxy-2-naphthalenesulfonic acid], disodium salt; 4,4'-[oxalylbis(imino-p-phenylenecarbonylimino)]bis[5-hydroxy-2-naphthalenesulfonic acid], disodium salt; 4,4'-[oxalylbis[(imino-6-methyl-3,1-phenylenecarbonyl)imino]]bis[5-hydroxy-2-naphthalenesulfonic acid], disodium salt; 4,4'-[oxalylbis[(imino-3-methyl-4,1-phenylenecarbonyl)imino]]bis[5-hydroxy-2-naphthalenesulfonic acid], disodium salt; 1,1'-[oxalylbis(imino-m-phenylenecarbonylimino)]bis[8-hydroxy-2-naphthalenesulfonic acid], disodium salt; 1,1'-[oxalylbis(imino-p-phenylenecarbonylimino)]bis[8-hydroxy-2-naphthalenesulfonic acid], disodium salt; 1,1'-[oxalylbis[(imino-6-methyl-3,1-phenylenecarbonyl)imino]]bis[8-hydroxy-2-naphthalenesulfonic acid], disodium salt; 1,1'-[oxalylbis[(imino-3-methyl-4,1-phenylenecarbonyl)imino]]bis[8-hydroxy-2-naphthalenesulfonic acid], disodium salt; 4,4'-[oxalylbis(imino-m-phenylenecarbonylimino)]bis[3-hydroxy-2-naphthalenesulfonic acid], disodium salt; 4,4'-[oxalylbis(imino-p-phenylenecarbonylimino)]bis[3-hydroxy-2-naphthalenesulfonic acid], disodium salt; 4,4'-[oxalylbis[(imino-6-methyl-3,1-phenylenecarbonyl)imino]]bis[3-hydroxy-2-naphthalenesulfonic acid], disodium salt; 4,4'-[oxalylbis[(imino-3-methyl-4,1-phenylenecarbonyl)imino]]bis[3-hydroxy-2-naphthalenesulfonic acid], disodium salt; 4,4'-[oxalylbis(imino-m-phenylenecarbonylimino)]bis[3-hydroxy-1-naphthalenesulfonic acid], disodium salt; 4,4'-[oxalylbis(imino-p-phenylenecarbonylimino)]bis[3-hydroxy-1-naphthalenesulfonic acid], disodium salt; 4,4'-[oxalylbis[(imino-6-methyl-3,1-phenylenecarbonyl)imino]]bis[3-hydroxy-1-naphthalenesulfonic acid], disodium salt; 4,4'-[oxalylbis[(imino-3-methyl-4,1-phenylenecarbonyl)imino]]bis[3-hydroxy-1-naphthalenesulfonic acid], disodium salt; 5,5'-[oxalylbis(imino-m-phenylenecarbonylimino)]bis[6-hydroxy-1-naphthalenesulfonic acid], disodium salt; 5,5'-[oxalylbis(imino-p-phenylenecarbonylimino)]bis[6-hydroxy-1-naphthalenesulfonic acid], disodium salt; 5,5'-[oxalylbis[(imino-6-methyl-3,1-phenylenecarbonyl)imino]]bis[6-hydroxy-1-naphthalenesulfonic acid], disodium salt; 5,5'-[oxalylbis[(imino-3-methyl-4,1-phenylenecarbonyl)imino]]bis[6-hydroxy-1-naphthalenesulfonic acid], disodium salt; 5,5'-[oxalylbis(imino-m-phenylenecarbonylimino)]bis[6-hydroxy-2-naphthalenesulfonic acid], disodium salt; 5,5'-[oxalylbis(imino-p-phenylenecarbonylimino)]bis[6-hydroxy-2-naphthalenesulfonic acid], disodium salt; 5,5'-[oxalylbis[(imino-6-methyl-3,1-phenylenecarbonyl)imino]]bis[6-hydroxy-2-naphthalenesulfonic acid], disodium salt; 5,5'-[oxalylbis[(imino-3-methyl-4,1-phenylenecarbonyl)imino]]bis[6-hydroxy-2-naphthalenesulfonic acid], disodium salt; 8,8'-[oxalylbis(imino-m-phenylenecarbonylimino)]bis[7-hydroxy-2-naphthalenesulfonic acid], disodium salt; 8,8'-[oxalylbis(imino-p-phenylenecarbonylimino)]bis[7-hydroxy-2-naphthalenesulfonic acid], disodium salt; 8,8'-[oxalylbis[(imino-6-methyl-3,1-phenylenecarbonyl)imino]]bis[7-hydroxy-2-naphthalenesulfonic acid], disodium salt; 8,8'-[oxalylbis[(imino-3-methyl-4,1-phenylenecarbonyl)imino]]bis[7-hydroxy-2-naphthalenesulfonic acid], disodium salt; 8,8'-[oxalylbis(imino-m-phenylenecarbonylimino)]bis[7-hydroxy-1-naphthalenesulfonic acid], disodium salt; 8,8'-[oxalylbis(imino-p-phenylenecarbonylimino)]bis[7-hydroxy-1-naphthalenesulfonic acid], disodium salt; 8,8'-[oxalylbis[(imino-6-methyl-3,1-phenylenecarbonyl)imino]]bis[7-hydroxy-1-naphthalenesulfonic acid], disodium salt; 8,8'-[oxalylbis[(imino-3-methyl-4,1-phenylenecarbonyl)imino]]bis[7-hydroxy-1-naphthalenesulfonic acid], disodium salt; 6,6'-[oxalylbis(imino-m-phenylenecarbonylimino)]bis[7-hydroxy-2-naphthalenesulfonic acid], disodium salt; 6,6'-[oxalylbis(imino-p-phenylenecarbonylimino)]bis[7-hydroxy-2-naphthalenesulfonic acid], disodium salt; 6,6'-[oxalylbis[(imino-6-methyl-3,1-phenylenecarbonyl)imino]]bis[7-hydroxy-2-naphthalenesulfonic acid], disodium salt; 6,6'-[oxalylbis[(imino-3-methyl-4,1-phenylenecarbonyl)imino]]bis[7-hydroxy-2-naphthalenesulfonic acid], disodium salt; 4,4'-[oxalylbis(imino-m-phenylenecarbonylimino)]bis[2-hydroxy-1-naphthalenesulfonic acid], disodium salt; 4,4'-[oxalylbis(imino-p-phenylenecarbonylimino)]bis[2-hydroxy-1-naphthalenesulfonic acid], disodium salt; 4,4'-[oxalylbis[(imino-6-methyl-3,1-phenylenecarbonyl)imino]]bis[2-hydroxy-1-naphthalenesulfonic acid], disodium salt; 4,4'-[oxalylbis[(imino-3-methyl-4,1-phenylenecarbonyl)imino]]bis[2-hydroxy-1-naphthalenesulfonic acid], disodium salt; 8,8'-[oxalylbis(imino-m-phenylenecarbonylimino)]bis[3-hydroxy-1-naphthalenesulfonic acid], disodium salt; 8,8'-[oxalylbis(imino-p-phenylenecarbonylimino)]bis[3-hydroxy-1-naphthalenesulfonic acid], disodium salt; 8,8'-[oxalylbis[(imino-6-methyl-3,1-phenylenecarbonyl)imino]]bis[3-hydroxy-1-naphthalenesulfonic acid], disodium salt; 8,8'-[oxalylbis[(imino-3-methyl-4,1-phenylenecarbonyl)imino]]bis[3-hydroxy-1-naphthalenesulfonic acid], disodium salt; 5,5'-[oxalylbis(imino-m-phenylenecarbonylimino)]bis[7-hydroxy-2-naphthalenesulfonic acid], disodium salt; 5,5'-[oxalylbis(imino-p-phenylenecarbonylimino)]bis[7-hydroxy-1-naphthalenesulfonic acid], disodium salt; 5,5'-[oxalylbis[(imino-6-methyl-3,1-phenylenecarbonyl)imino]]bis[7-hydroxy-2-naphthalenesulfonic acid], disodium salt; 5,5'-[oxalylbis[(imino-3-methyl-4,1-phenylenecarbonyl)imino]]bis[7-hydroxy-2-naphthalenesulfonic acid], disodium salt; 4,4'-[oxalylbis(imino-m-phenylenecarbonylimino)]bis[7-hydroxy-2-naphthalenesulfonic acid], disodium salt; 4,4'-[oxalylbis(iminop-phenylenecarbonylimino)]bis[7-hydroxy-2-naphthalenesulfonic acid], disodium salt; 4,4'-[oxalylbis[(imino-6-methyl-3,1-phenylenecarbonyl)imino]]bis[7-hydroxy-2-naphthalenesulfonic acid], disodium salt; 4,4'-[oxalylbis[(imino-3-methyl-4,1-phenylenecarbonyl)imino]]bis[7-hydroxy-2-naphthalenesulfonic acid], disodium salt; 4,4'-[oxalylbis(imino-m-phenylenecarbonylimino)]bis[7-hydroxy-1-naphthalenesulfonic acid], disodium salt; 4,4'-[oxalylbis(imino-p-phenylenecarbonylimino)]bis[7-hydroxy-1-naphthalenesulfonic acid], disodium salt; 4,4'-[oxalylbis[(imino-6-methyl-3,1-phenylenecarbonyl)imino]]bis[7-hydroxy-1-naphthalenesulfonic acid], disodium salt; 4,4'-[oxalylbis[(imino-3-methyl-4,1-phenylenecarbonyl)imino]]bis[7-hydroxy-1-naphthalenesulfonic acid], disodium salt; 7,7'-[oxalylbis(imino-m-phenylenecarbonylimino)]bis[3-hydroxy-1-naphthalenesulfonic acid], disodium salt; 7,7'-[oxalylbis(imino-p-phenylenecarbonylimino)]bis[3-hydroxy-1-naphthalenesulfonic acid], disodium salt; 7,7'-[oxalylbis[(imino-6-methyl-3,1-phenylenecarbonyl)imino]]bis[3-hydroxy-1-naphthalenesulfonic acid], disodium salt; 7,7'-[oxalylbis[(imino-3-methyl-4,1-phenylenecarbonyl)imino]]bis[3-hydroxy-1-naphthalenesulfonic acid], disodium salt; 3,3'-[oxalylbis(imino-m-phenylenecarbonylimino)]bis[7-hydroxy-1-naphthalenesulfonic acid], disodium salt; 3,3'-[oxalylbis(imino-p-phenylenecarbonylimino)]bis[7-hydroxy-1-naphthalenesulfonic acid], disodium salt; 3,3'-[oxalylbis[(imino-6-methyl-3,1-phenylenecarbonyl)imino]]bis[7-hydroxy-1-naphthalenesulfonic acid], disodium salt; 3,3'-[oxalylbis[(imino-3-methyl-4,1-phenylenecarbonyl)imino]]bis[7-hydroxy-1-naphthalenesulfonic acid], disodium salt; 6,6'-[oxalylbis(imino-m-phenylenecarbonylimino)]bis[3-hydroxy-2-naphthalenesulfonic acid], disodium salt; 6,6'-[oxalylbis(imino-p-phenylenecarbonylimino)]bis[3-hydroxy-2-naphthalenesulfonic acid], disodium salt; 6,6'-[oxalylbis[(imino-6-methyl-3,1-phenylenecarbonyl)imino]]bis[3-hydroxy-2-naphthalenesulfonic acid], disodium salt; 6,6'-[oxalylbis[(imino-3-methyl-4,1-phenylenecarbonyl)imino]]bis[3-hydroxy-2-naphthalenesulfonic acid], disodium salt; 3,3'-[oxalylbis(imino-m-phenylenecarbonylimino)]bis[6-hydroxy-2-naphthalenesulfonic acid], disodium salt; 3,3'-[oxalylbis(imino-p-phenylenecarbonylimino)]bis[6-hydroxy-2-naphthalenesulfonic acid], disodium salt; 3,3'-[oxalylbis[(imino-6-methyl-3,1-phenylenecarbonyl)imino]]bis[6-hydroxy-2-naphthalenesulfonic acid], disodium salt; 3,3'-[oxalylbis[(imino-3-methyl-4,1-phenylenecarbonyl)imino]]bis[6-hydroxy-2-naphthalenesulfonic acid], disodium salt; 4,4'-[oxalylbis(imino-m-phenylenecarbonylimino)]bis[6-hydroxy-1-naphthalenesulfonic acid], disodium salt; 4,4'-[oxalylbis(imino-p-phenylenecarbonylimino)]bis[6-hydroxy-1-naphthalenesulfonic acid], disodium salt; 4,4'-[oxalylbis[(imino-6-methyl-3,1-phenylenecarbonyl)imino]]bis[6-hydroxy-1-naphthalenesulfonic acid], disodium salt; 4,4'-[oxalylbis[(imino-3-methyl-4,1-phenylenecarbonyl)imino]]bis[6-hydroxy-1-naphthalenesulfonic acid], disodium salt; 5,5'-[oxalylbis(imino-m-phenylenecarbonylimino)]bis[3-hydroxy-1-naphthalenesulfonic acid], disodium salt; 5,5'-[oxalylbis(imino-p-phenylenecarbonylimino)]bis[3-hydroxy-1-naphthalenesulfonic acid], disodium salt; 5,5'-[oxalylbis[(imino-6-methyl-3,1-phenylenecarbonyl)imino]]bis[3-hydroxy-1-naphthalenesulfonic acid], disodium salt; 5,5'-[oxalylbis[(imino-3-methyl-4,1-phenylenecarbonyl)imino]]bis[3-hydroxy-1-naphthalenesulfonic acid], disodium salt; 4,4'-[oxalylbis(imino-m-phenylenecarbonylimino)]bis[6-hydroxy-2-naphthalenesulfonic acid], disodium salt; 4,4'-[oxalylbis(imino-p-phenylenecarbonylimino)]bis[6-hydroxy-2-naphthalenesulfonic acid], disodium salt; 4,4'-[oxalylbis[(imino-6-methyl-3,1-phenylenecarbonyl)imino]]bis[6-hydroxy-2-naphthalenesulfonic acid], disodium salt; 4,4'-[oxalylbis[(imino-3-methyl-4,1-phenylenecarbonyl)imino]]bis[6-hydroxy-2-naphthalenesulfonic acid], disodium salt; 4,4'-[oxalylbis(imino-m-phenylenecarbonylimino)]bis[3-hydroxy-1-naphthalenesulfonic acid], diacetate (diester); 4,4'-[oxalylbis(imino-p-phenylenecarbonylimino)]bis[3-hydroxy-1-naphthalenesulfonic acid], diacetate (diester); 4,4'-[oxalylbis[(imino-6-methyl-3,1-phenylenecarbonyl)imino]]bis[3-hydroxy-1-naphthalenesulfonic acid], diacetate (diester); 4,4'-[oxalylbis[(imino-3-methyl-4,1-phenylenecarbonyl)imino]]bis[3-hydroxy-1-naphthalenesulfonic acid], diacetate (diester); 6,6'-[oxalylbis(imino-P-phenylenydroxy-2-naphthalenesulfonic acid]tetrasodium salt; 6,6'-[oxalylbis(imino-M-phenylenecarbonylimino)]bis[4-hydroxy-2-naphthalenesulfonic acid]tetrasodium salt; 6,6'-[oxalylbis(imino-4-methyl-3,1-phenylene)carbonylimino]bis[4-hydroxy-2-naphthalenesulfonic acid]disodium salt; and 6,6'-[oxalylbis(imino-3-methyl-4,1-phenylene)carbonylimino]bis(4-hydroxy-2-naphthalenesulfonic acid]disodium salt.

This invention is also concerned with a method of inhibiting connective tissue destruction in a warm-blooded animal which comprises administering to said animal an effective inhibiting amount of a compound encompassed within Formulae I, II, III or IV. Moreover, this invention is concerned with a method of inhibiting the degradation sequelae of collagenase activity in a body fluid, such as crevicular fluid, synovial fluid and the like, which comprises subjecting body fluid collagenase to the action of an effective collagenase inhibiting amount of a compound encompassed within the above formulae. Body fluid can include blood, plasma, serum, synovial fluid, crevicular fluid, ocular fluid, etc., containing collagenase. The method of use aspect of this invention is further concerned with a method of inhibiting the action of collagenase in a warm-blooded animal which comprises internally administering to said animal an effective collagenase inhibiting amount of a compound encompassed with the above formulae.

A further method of use aspect of the present invention is concerned with a method for inhibiting and preventing the deposition of dental plaque onto the surfaces of the teeth of warm-blooded animals, mainly, the deposition of dental plaque onto human teeth, which comprises applying the potential plaque barrier [oxalylbis(iminophenylenecarbonylimino)]bis[hydroxynaphthalenesulfonic acids] and salts thereof of the present invention, which are substantially soluble in water or water/organic solvent vehicles, in the form of various dentifrice formulations such as pastes, ointments, creams, lotions, gels, powders, buccal tablets, lozenges, tooth paste, rinses and the like or other oral hygienic procedures.

The compounds of the present invention find utility as inhibitors of connective tissue destruction or as collagenase inhibitors in body fluids. As such they may be useful in ameliorating or preventing those pathological reactions resulting from the functioning of collagenase, and in the therapeutic treatment of warm-blooded animals having connective tissue disorders such as periodontal diseases and diseases of the teeth, osteoporosis, osteolysis, Paget's disease, hyperparathyroidism of renal failure, rheumatoid arthritis, septic arthritis, osteoarthritis, gout, acute synovitis, scleroderma, psoriasis, epidermolysis bullosa, keloids, blisters, cholesteatoma of the ear, and corneal ulceration. The compounds of the present invention may also be useful in those pathological states where excessive activity of neutral proteases causes tissue damage.

DETAILED DESCRIPTION OF THE INVENTION

The compounds of the present invention may be prepared according to the following Flowchart A.

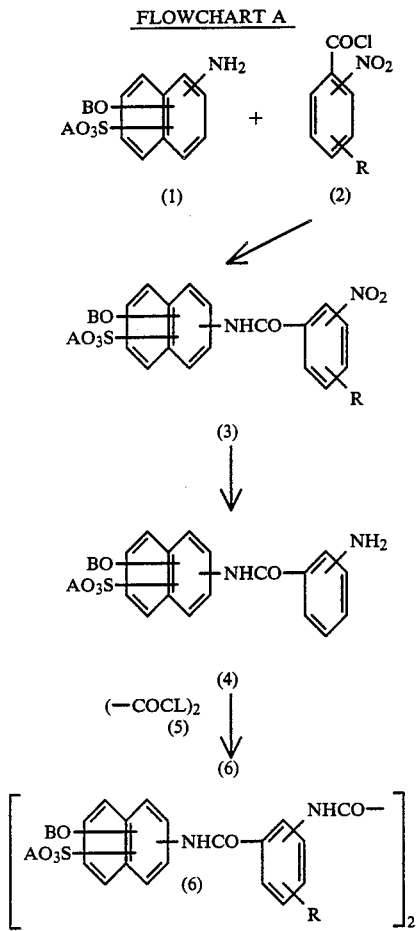

With reference to Flowchart A, a substituted-aminonaphthalenemonosulfonic acid (1) is dissolved in water, made basic with any suitable base such as, for example, an alkali acetate or alkali metal carbonate, reacted with an alkali acetate such as sodium acetate, filtered and reacted under an inert atmosphere, e.g., nitrogen, with an excess of substituted nitrobenzoyl chloride (2), giving a substituted nitrobenzamido-substituted-naphthalenesulfonic acid (3). This nitro derivative (3) is then hydrogenated in the presence of a suitable catalyst, giving the corresponding amine derivative (4). The amine derivative (4) is heated in the presence of solvents such as hexamethylphosphoramide and pyridine to achieve solution. The filtered solution is chilled and treated by the dropwise addition of oxalyl chloride (5) in a solvent such as toluene. After stirring at room temperature, filtration and concentration gives a residue which is treated with ethanol, then ether. The residue is suspended in water, made basic with a suitable base, then filtered. The filtrate is adjusted to pH 4 with acetic acid and poured into ethanol-ether. Filtration and washing with ethanol-ether gives the oxalyldiimide compound (6).

The following Examples will serve to illustrate the invention in more detail and should not be construed to limit the scope of the invention in any way.

EXAMPLE 1

Amine Precursor 6-(m-Aminobenzamido)-4-hydroxy-2-naphthalenesulfonic acid-zwitterionic compound To a suspension of 180 g of 6-amino-4-hydroxy-2-naphthalenesulfonic acid in 4 liters of water was added 75 ml of 10N sodium hydroxide. To the resulting solution was added 181.8 g of sodium acetate trihydrate, followed by 190 g of m-nitrobenzoyl chloride. The mixture was stirred vigorously under argon at room temperature for 8 hours and then filtered. The solid was washed with water, ethanol and then ether and dried at room temperature. The resulting brown solid (299.4 g) was added to a mixture of 1500 ml of water and 1200 ml of 1N sodium hydroxide and stirred under argon for one hour. The mixture was filtered and the filtrate was acidified to pH 3 with concentrated hydrochloric acid. The resulting precipitate was collected by filtration, washed with water, ethanol, then ether and dried in vacuo in hot water and gave 221.7 g of 4-hydroxy-6-m-nitrobenzamido-2-naphthalenesulfonic acid, sodium salt.

To a suspension of 150 g of 4-hydroxy-6-m-nitrobenzamido-2-naphthalenesulfonic acid, sodium salt in 1200 ml of water was added sufficient 10N sodium hydroxide to effect solution. The solution was filtered, then hydrogenated in a Parr shaker using 10% palladium-on-carbon catalyst. The reaction mixture was filtered through diatomaoeous earth, diluted with water and the filtrate was acidified with concentrated hydrochloric acid. The resulting solid was collected by filtration, washed with water, ethanol, then ether and dried in vacuo for 16 hours at room temperature to give 108 g of 6-(m-aminobenzamido)-4-hydroxy-2-naphthalenesulfonic acid-zwitterionic compound.

EXAMPLE 2

6,6'-[Oxalylbis(imino-m-phenylenecarbonylimino)]bis-[4-hydroxy-2-naphthalenesulfonic acid]disodium salt A mixture of 2.55 g of the product of Example 1, 125 ml of dried hexamethylphosphoramide and 2.12 ml of pyridine was heated on a steam bath (under a calcium chloride drying tube) until solution was achieved. The solution was filtered and the filtrate was chilled in an ice bath. Then a solution of 0.55 ml of oxalyl chloride in 8.0 ml of dried toluene was added dropwise over a 15 minute period with stirring. The dropping funnel was washed with one ml of dried toluene which added to the mixture. The ice bath was removed and the mixture was stirred at room temperature for 1.5 hours, then added 5.0 ml of water and stirred for one hour longer. The mixture was filtered and the filtrate was concentrated in vacuo at a water bath temperature of 100° C. The residue was triturated with 150 ml of ethanol and stirred for one hour. The mixture was filtered, washed with ethanol then ether and dried to yield 2.0 g (A) of solid material. An additional 0.4 g (B) of solid was recovered from the above ether wash.

The combined solid (A+B) 2.4 g was dissolved in 70 ml of hexamethylphosphoramide by warming, then the oxalyl chloride addition step was repeated as hereinabove described using the same quantities. Work-up and filtration as described above gave 1.5 g (C) of solid material, plus an additional 0.9 g (D) of solid obtained by adding ether to the above filtrate.

The preceding crops (C and D), 2.4 g were combined and dissolved in 25–30 ml of water and the pH adjusted to pH 9.5 with sodium hydroxide. The mixture was filtered and poured slowly into 350 ml of ethanol:ether (1:1) with vigorous stirring. The resulting yellow solid was collected by filtration, washed with ethanol:ether (1:1), then with ether and dried to give 1.8 g of material.

A 1.6 g amount of the above material in 30 ml of water was adjusted to pH 5–6 with acetic acid giving a semi-gel. This semi-gel was poured into 750 ml of ethanol:ether (1:1) and filtered. The solid was washed with ethanol:ether (2:1), then ether and dried giving 1.6 g of a brown solid.

The brown solid was suspended in 40 ml of water and the pH was adjusted to pH 5–6 with acetic acid. The mixture was heated on a steam bath then was poured into 800 ml of ethanol:ether (1:1) with vigorous stirring. The solid was collected, washed with ethanol:ether (2:1), then with ether and dried to give 1.5 g of material.

The preceding material was then suspended in 25–30 ml of water and adjusted to pH 4.0 with glacial acetic acid. This solution was poured into 600 ml of ethanol:ether (1:1). The precipitate was collected by filtration, washed with 150 ml of ethanol:ether (2:1), then ether and dried and gave 1.3 g of the product of the Example.

EXAMPLE 3

Preparation of Compressed Tablet

| Ingredient | mg./Tablet |
| --- | --- |
| Active Compound | 0.5–500 |
| Dibasic Calcium Phosphate N.F. | qs |
| Starch USP | 40 |
| Modified Starch | 10 |
| Magnesium Stearate USP | 1–5 |

EXAMPLE 4

Preparation of Compressed Tablet—Sustained Action

| Ingredient | mg./Tablet |
| --- | --- |
| Active Compound as Aluminum Lake*, Micronized | 0.5–500 (as acid equivalent) |
| Dibasic Calcium Phosphate N.F. | qs |
| Alginic Acid | 20 |
| Starch USP | 35 |
| Magnesium Stearate USP | 1–10 |

*Complement inhibitor plus aluminum sulfate yields aluminum complement inhibitor. Complement inhibitor content in aluminum lake ranges from 5–30%.

EXAMPLE 5

Preparation of Hard Shell Capsule

| Ingredient | mg./Capsule |
| --- | --- |
| Active Compound | 0.5–500 |
| Lactose, Spray Dried | qs |
| Magnesium Stearate | 1–10 |

EXAMPLE 6

Preparation of Oral Liquid (Syrup)

| Ingredient | % W/V |
| --- | --- |
| Active Compound | 0.05–5 |
| Liquid Sugar | 75.0 |
| Methyl Paraben USP | 0.18 |
| Propyl Paraben USP | 0.02 |
| Flavoring Agent | qs |
| Purified Water qs ad | 100.0 |

EXAMPLE 7

Preparation of Oral Liquid (Elixir)

| Ingredient | % W/V |
| --- | --- |
| Active Compound | 0.05–5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 8

Preparation of Oral Suspension (Syrup)

| Ingredient | % W/V |
| --- | --- |
| Active Compound as Aluminum Lake, Micronized | 0.05–5 (acid equivalent) |
| Polysorbate 80 USP | 0.1 |
| Magnesium Aluminum Silicate, Colloidal | 0.3 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

EXAMPLE 9

Preparation of Injectable Solution

| Ingredient | % W/V |
| --- | --- |
| Active Compound | 0.05–5 |
| Benzyl Alcohol N.F. | 0.9 |
| Water for Injection qs ad | 100.0 |

EXAMPLE 10

Preparation of Injectable Oil

| Ingredient | % W/V |
| --- | --- |
| Active Compound | 0.05–5 |
| Benzyl Alcohol | 1.5 |
| Sesame Oil qs ad | 100.0 |

EXAMPLE 11

Preparation of Intra-Articular Product

| Ingredient | Amount |
| --- | --- |
| Active Compound | 2–20 mg. |
| NaCl (physiological saline) | 0.9% |
| Benzyl Alcohol | 0.9% |

-continued

| Ingredient | Amount |
|---|---|
| Sodium Carboxymethylcellulose | 1–5% |
| pH adjusted to 5.0–7.5 | |
| Water for Injection qs ad | 100% |

EXAMPLE 12

Preparation of Injectable Depo Suspension

| Ingredient | % W/V |
|---|---|
| Active Compound | 0.05–5 |
| | (acid equivalent) |
| Polysorbate 80 USP | 0.2 |
| Polyethylene Glycol 4000 USP | 3.0 |
| Sodium Chloride USP | 0.8 |
| Benzyl Alcohol N.F. | 0.9 |
| HCl to pH 6–8 | qs |
| Water for Injection qs ad | 100.0 |

EXAMPLE 13

Preparation of Dental Paste

| Ingredient | % W/V |
|---|---|
| Active Compound | 0.05–5 |
| Zinc Oxide | 15 |
| Polyethylene Glycol 4000 USP | 50 |
| Distilled Water qs ad | 100 |

EXAMPLE 14

Preparation of Dental Ointment

| Ingredient | % W/W |
|---|---|
| Active Compound | 0.05–5 |
| Petrolatum, White USP qs | 100 |

EXAMPLE 15

Preparation of Dental Cream

| Ingredient | % W/W |
|---|---|
| Active Compound | 0.05–5 |
| Mineral Oil | 50 |
| Beeswax | 15 |
| Sorbitan Monostearate | 2 |
| Polyoxyethylene 20 Sorbitan Monostearate | 3 |
| Methyl Paraben USP | 0.18 |
| Propyl Paraben USP | 0.02 |
| Distilled Water qs | 100 |

EXAMPLE 16

Preparation of Topical Cream

| Ingredient | % W/W |
|---|---|
| Active Compound | 0.05–5 |
| Sodium Lauryl Sulfate | 1 |
| Propylene Glycol | 12 |
| Stearyl Alcohol | 25 |
| Petrolatum, White USP | 25 |
| Methyl Paraben USP | 0.18 |
| Propyl Paraben USP | 0.02 |

-continued

| Ingredient | % W/W |
|---|---|
| Purified Water qs | 100 |

EXAMPLE 17

Preparation of Topical Ointment

| Ingredient | % W/W |
|---|---|
| Active Compound | 0.05–5 |
| Cholesterol | 3 |
| Stearyl Alcohol | 3 |
| White Wax | 8 |
| Petrolatum, White USP qs | 100 |

EXAMPLE 18

Preparation of Spray Lotion (Non-aerosol)

| Ingredient | % W/W |
|---|---|
| Active Compound | 0.05–5 |
| Isopropyl Myristate | 20 |
| Alcohol (Denatured) qs | 100 |

EXAMPLE 19

Preparation of Buccal Tablet

| Ingredient | g./Tablet |
|---|---|
| Active Ingredient | 0.00325 |
| 6 × Sugar | 0.29060 |
| Acacia | 0.01453 |
| Soluble Starch | 0.01453 |
| F. D. & C. Yellow No. 6 Dye | 0.00049 |
| Magnesium Stearate | 0.00160 |
| | 0.32500 |

The final tablet will weigh about 325 mg. and may be compressed into buccal tablets in flat faced or any other tooling shape convenient for buccal administration.

EXAMPLE 20

Preparation of Lozenge

| Ingredient | g./Lozenge |
|---|---|
| Active Ingredient | 0.0140 |
| Kompact ® Sugar (Sucrest Co.) | 0.7138 |
| 6 × Sugar | 0.4802 |
| Sorbitol (USP Crystalline) | 0.1038 |
| Flavor | 0.0840 |
| Magnesium Stearate | 0.0021 |
| Dye | qs |
| Stearic Acid | 0.0021 |
| | 1.4000 |

The ingredients are compressed into $\frac{5}{8}$" flat based lozenge tooling. Other shapes may also be utilized.

EXAMPLE 21

Preparation of Gelled Vehicles

| Ingredient | % W/W |
|---|---|
| Active Compound | 9–11 |
| Sodium Chloride | 0.9–1.2 |
| Buffer and Flavor qs | — |

-continued

| Ingredient | % W/W |
|---|---|
| Purified Water qs ad | 100 |
| Active Compound | 0.005-9 |
| Sodium Alginate | 0.5-2 |
| Buffer and Flavor qs | — |
| Purified Water qs ad | 100 |
| Active Compound | 0.005-9 |
| Hydroxypropyl Cellulose | 0.5-2 |
| Buffer and Flavor qs | — |
| Purified Water qs ad | 100 |
| Active Compound | 0.005-9 |
| Guar Gum | 0.5-2 |
| Buffer and Flavor qs | — |
| Purified Water qs ad | 100 |

EXAMPLE 22

Preparation of Oral Mouth Rinse

| Ingredient | % W/V |
|---|---|
| Active Compound | 0.05-20 |
| Alcohol U.S.P. | 0-20 |
| Sorbitol | 1-30 |
| Buffer and Flavor qs | — |
| Polysorbate 80 | 0.1-3 |
| Cetyl Pyridinium Chloride | 0.025-0.20 |
| Purified Water qs ad | 100 |

EXAMPLE 23

Preparation of Tooth Paste

| Ingredient | % W/W |
|---|---|
| Active Compound | 0.05-15 |
| Glycerin | 5-15 |
| Sorbitol | 5-15 |
| Sodium Carboxymethylcellulose | 0.5-2 |
| Magnesium Aluminum Silicate | 0.1-1 |
| Carrageenin | 0.25-2 |
| Preservative qs | — |
| Sodium Lauryl Sulfate | 0.1-3 |
| Calcium Carbonate | 25-45 |
| Flavor qs | — |
| Purified Water qs ad | 100 |

EXAMPLE 24

Preparation of Dental Paste

| Ingredient | % W/W |
|---|---|
| Active Compound | 0.05-20 |
| Carboxymethylcellulose | 5-20 |
| Pectin | 5-20 |
| Plastibase ® | 20-70 |
| Gelatin | 5-20 |

EXAMPLE 25

Preparation of Dental Ointment

| Ingredient | % W/W |
|---|---|
| Active Compound | 0.05-20 |
| Polyethylene Glycol 4000 | 50-80 |
| Polyethylene Glycol 400 | 10-40 |

EXAMPLE 26

Preparation of Dental Powder for Brushing or for Use in Water Spray (e.g. Water Pik ®)

| Ingredient | % W/W |
|---|---|
| Active Compound | 0.05-10 |
| Flavor qs | — |
| Wetting Agents qs | — |
| Dextrin qs ad | 100 |

EXAMPLE 27

Preparation of Stick for Application to Gums

| Ingredient | % W/W |
|---|---|
| Active Compound | 0.05-10 |
| Glycerin | 5-10 |
| Propylene Glycol | 40-80 |
| Sodium Stearate | 6-10 |
| Flavor qs | — |
| Water | 0-10 |

EXAMPLE 28

Preparation of Periodontal Packing Paste

| Ingredient | % W/W |
|---|---|
| Paste Part A | |
| Active Compound | 0.05-20 |
| Caprylic Acid | 9.0 |
| Lauric Acid | 27.0 |
| Ethylcellulose (100 cps.) | 2.0 |
| Polypale Resin* | 39.0 |
| Gum Elemi | 4.0 |
| Brominol** | 4.0 |
| Mica (powdered) | 7.5 |
| Chlorothymol | 1.0 |
| Zinc Acetate | 2.0 |
| Bay Oil (essential oil) | 1.0 |
| Ethanol | 1.5 |
| Paste Part B | |
| Magnesium Oxide | 43.0 |
| Zinc Oxide | 21.0 |
| Calcium Hydroxide | 3.5 |
| Copper Oxide | 2.0 |
| Mineral Oil, Heavy | 26.0 |
| Rosin Oil | 3.0 |
| Chlorothymol | 1.4 |
| Cumarin (flavor) | 0.1 |

*Partially polymerized rosin (i.e. modified rosin)
**Brominated olive oil

When equal parts of A and B are mixed together at 25° C. a hard mass is formed in about 3 minutes.

EXAMPLE 29

Preparation of Periodontal Packing Paste

| Ingredient | % W/W |
|---|---|
| Part A (powder) | |
| Active Compound | 0.05-20 |
| Canada Balsam, Neutral | 8.5 |
| Rosin NF | 8.5 |
| Calcium Hydroxide | 34.4 |
| Zinc Oxide U.S.P. | 46.0 |
| Part B (Liquid Hardener) | |
| Eugenol | 85.0 |
| Turpentine Oil, Rectified | 15.0 |

A mixture of three drops of Part B added to 130 mg of Part A produces a hard mass in about 2-3 minutes at 30° C.

The compounds of this invention may be administered internally to a warm-blooded animal to inhibit connective tissue destruction or collagenase, such inhibition being useful in the amelioration or prevention of those reactions causing connective tissue damage. A range of doses may be employed depending on the mode of administration, the condition being treated and the particular compound being used. For example, for intravenous or subcutaneous use from about 5 to about 50 mg/kg/day, or every six hours for more rapidly excreted salts, may be used. For intra-articular use for large joints such as the knee, from about 2 to about 20 mg/joint per week may be used, with proportionally smaller doses for smaller joints. The dosage range is to be adjusted to provide optimum therapeutic response in the warm-blooded animal being treated. In general, the amount of compound administered can vary over a wide range to provide from about 1.5 mg/kg to about 100 mg/kg of body weight of animal per day. The usual daily dosage for a 70 kg subject may vary from about 100 mg to about 3.5 g. Unit doses can contain from about 0.5 mg to about 500 mg.

While in general the sodium salts of the acids of the invention are suitable for parenteral use, other salts may also be prepared, such as those of primary amines, e.g., ethylamine; secondary amines, e.g., diethylamine or diethanolamine; tertiary amines, e.g., pyridine or triethylamine or 2-dimethylaminomethyldibenzofuran, aliphatic diamines, e.g., decamethylenediamine; and aromatoic diamines, can be prepared. Some of these are soluble in water, others are soluble in saline solution, and still others are insoluble and can be used for purposes of preparing suspensions for injection. Furthermore, as well as the sodium salt, those of the alkali metals, such as potassium and lithium; of ammonia; and of the alkaline earth metals, such as calcium or magnesium, may be employed. It will be apparent, therefore, that these salts embrace, in general, derivatives of salt-forming cations.

In therapeutic use the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e., oral or parenteral.

The compounds of this invention can be used in compositions such as tablets. Here, the principal active ingredient is mixed with conventional tabletting ingredients such as corn starch, lactose, sucrose, sorbitol, talc, stearic acid, magnesium stearate, dicalcium phosphate, gums, or similar materials as non-toxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate non-toxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The compounds of the present invention may also be administered topically in the form of ointments, creams, lotions and the like, suitable for the treatment of connective tissue dependent dermatological disorders.

Moreover, the compounds of the present invention may be administered in the form of dental pastes, ointments, buccal tablets and other compositions suitable for application periodontally for the treatment of periodontitis and related diseases of the oral cavity.

The term dosage form as described herein refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The inhibiting activity of a representative compound of the invention on the destruction of connective tissue has been demonstrated by the following identified test:

(i) *Collagenase Assay, Test Code* 006—This test measures the ability of human skin fibroblast collagenase to degrade radiolabled native collagen fibrils. An active inhibitor inhibits the degradation of the collagen fibril.

(i) Collagenase Assay—Test Code 006

A collagenase assay was performed by a modification of the method of Harper, et al., *Biochem.*, 10, 3035 (1971). In a typical assay (total volume of 0.45 ml), 100 $\mu$l of the activated enzyme was added to the $^{14}$C-labeled collagen fibrils (250 $\mu$l) followed by 100 $\mu$l of 50 mM cacodylate, pH 7.4, containing 5 mM calcium chloride. After incubation at 37° C. for 16 hours, the tubes were centrifuged in a Beckman microfuge for five minutes at full speed. An aliquot (200 $\mu$l) of the supernatant, representing collagenase digestion products of the fibril, was assayed for radioactivity. The effect of the test compound on collagen degradation by collagenase was examined as follows:

Varying concentrations of the test compound (in distilled water) were added to the assay tubes containing active collagenase (total volume 450 μl) and after 16 hours the amount of radioactivity in the supernatant was determined. Appropriate blanks and trypsin controls were run in parallel.

Table I shows that a representative compound of the invention possesses the ability to inhibit collagen degradation. The result is expressed as an $ID_{50}$ collagenase value which represents a ratio of the weight (μg) of the representative compound required for 50% inhibition of collagenase over the weight (μg) of 6,6,-[ureylenebis(m-phenylenecarbonylimino)]bis[4-hydroxy-2-naphthalenesulfonic acid]disodium salt required for 50% inhibition of collagenase. The compound 6,6'-[ureylenebis(m-phenylenecarbonylimino]bis[4-hydroxy-2-naphthalenesulfonic acid]disodium salt has been established as an inhibitor of the degradation of collagen in U.S. Pat. No. 4,297,372. An $ID_{50}$ collagenase ratio of one indicates that the compound is as efficient as the reference compound in inhibiting collagen degradation. A value greater than one indicates that the test compound is less active.

TABLE I

| Compound | Biological Activity (test conc.: 30 μg/ml) $ID_{50}$ Collagenase Ratio |
|---|---|
| 6,6'-[Oxalylbis(imino-m-phenylenecarbonylimino)]bis[4-hydroxy-2-naphthalenesulfonic acid]disodium salt | 1.10 |

Binding Assay

It has been shown that 6,6'-[ureylenebis(m-phenylenecarbonylimino)]bis[4-hydroxy-2-naphthalenesulfonic acid]disodium salt will bind to insoluble collagenous structures such as teeth, dentin, gingiva and the like. This binding is saturable and reversible.

Using (radioactive) $^{14}$C-6,6'-[ureylenebis(m-phenylenecarbonylimino)]bis[4-hydroxy-2-naphthalenesulfonic acid]disodium salt a binding (competition) assay procedure is established which involves an insoluble substrate such as tooth powder which will bind the $^{14}$C-6,6'-[ureylenebis(m-phenylenecarbonylimino)]-bis[4-hydroxy-2-naphthalenesulfonic acid]disodium salt. The amount of $^{14}$C-6,6'-[ureylenebis(m-phenylenecarbonylimino)]bis[4-hydroxy-2-naphthalenesulfonic acid]disodium salt bound is determined by washing away the unbound radioactive compound and counting CPM (counts per minute) of the insoluble tooth powder/$^{14}$C-6,6'-[ureylenebis(m-phenylenecarbonylimino)]bis[4-hydroxy-2-naphthalenesulfonic acid]disodium salt complex. The assay may be used to determine the ability of a competing analog of 6,6'-[ureylenebis(m-phenylenecarbonylimino)]bis[4-hydroxy-2-naphthalenesulfonic acid]disodium salt to inhibit binding in the following manner: $^{14}$C-6,6'-[ureylenebis(m-phenylenecarbonylimino)]bis[4-hydroxy-2-naphthalenesulfonic acid]disodium salt and a non-radioactive analog thereof were incubated with tooth powder. The inhibiting effect of the test compound on binding compared to non-radioactive 6,6'-[ureylenebis(m-phenylenecarbonylimino)]bis[4-hydroxy-2-naphthalenesulfonic acid]disodium salt was determined as follows: A one mg amount of tooth powder was incubated in one ml of phosphate buffered saline (PBS) with 10 μg of $^{14}$C-6,6'-[ureylenebis(m-phenylenecarbonylimino)]bis[4-hydroxy-2-naphthalenesulfonic acid]disodium salt and varying dose amounts (ranging from 0 to 2 mg) of the same cold (non-radioactive) compound. After 60 minutes at 37° C., the unbound radioactive compound was washed away and the amount of radioactivity bound to the tooth powder was determined for each dose by counting (CPM). The dose in μg of cold compound required to decrease the amount of radioactive agent by 50% ($ID_{50}$) was determined. Then varying amounts of the test compound were substituted for cold 6,6'-[ureylenebis(m-phenylenecarbonylimino)]bis[4-hydroxy-2-naphthalenesulfonic acid]disodium salt in the above assay and the $ID_{50}$ for this compound was determined.

An $ID_{50}$ ratio provides a biological comparison of all compounds as established by use of the following equation:

$$ID_{50} \text{ Binding Ratio} = \frac{\text{Dose (μg) of test compound required to decrease } ^{14}\text{C-binding to 50\%}}{\text{Dose (μg) of cold 6,6'-[ureylenebis(m-phenylenecarbonylimino)]bis[4-hydroxy-2-naphthalenesulfonic acid]disodium salt required to decrease } ^{14}\text{C-binding to 50\%}}$$

Results of this test on a representative compound of the present invention appear in Table II.

TABLE II

| Compound | $ID_{50}$ Binding Ratio |
|---|---|
| 6,6'-[Oxalylbis(imino-m-phenylenecarbonylimino)]bis[4-hydroxy-2-naphthalenesulfonic acid]disodium salt | 1.00 |

An $ID_{50}$ binding ratio of one indicates that the compound is as efficient as the reference compound in competition for binding sites in tooth powder. Values greater than one indicate the compound is less efficient than the reference compound.

We claim:

1. A compound of the formula:

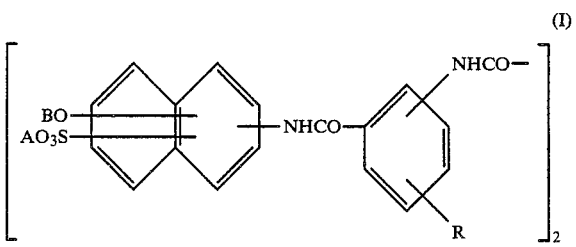

wherein A is hydrogen or a pharmaceutically acceptable salt cation; B is hydrogen, lower($C_1$–$C_6$)alkanoyl or alkali metal; and R is hydrogen or lower($C_1$–$C_3$)alkyl.

2. A compound according to claim 1 of the formula:

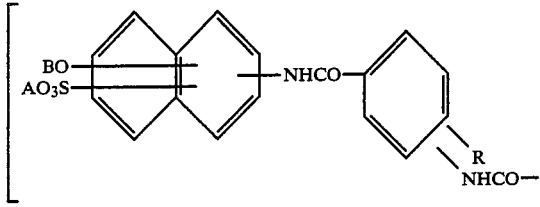

wherein A is hydrogen or a pharmaceutically acceptable salt cation; B is hydrogen, lower($C_1$–$C_6$)alkanoyl or alkali metal; and R is hydrogen or lower($C_1$–$C_3$)alkyl.

3. A compound according to claim 1 of the formula:

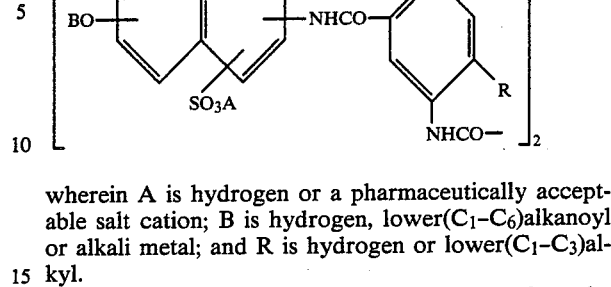

wherein A is hydrogen or a pharmaceutically acceptable salt cation; B is hydrogen, lower($C_1$–$C_6$)alkanoyl or alkali metal; and R is hydrogen or lower($C_1$–$C_3$)alkyl.

4. A compound according to claim 1 of the formula:

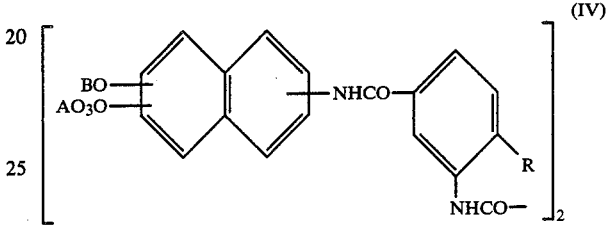

wherein A is hydrogen or a pharmaceutically acceptable salt cation; B is hydrogen, lower($C_1$–$C_6$)alkanoyl or alkali metal; and R is hydrogen or lower($C_1$–$C_3$)alkyl.

5. The compound according to claim 1; 6,6'-[oxalyl-bis(imino-m-phenylenecarbonylimino)]bis[4-hydroxy-2-naphthalenesulfonic acid]disodium salt.

* * * * *